United States Patent [19]

Ankeny et al.

[11] Patent Number: 5,157,959
[45] Date of Patent: Oct. 27, 1992

[54] AUTOMATED PONDED INFILTROMETER

[75] Inventors: Mark D. Ankeny, Albuquerque, N. Mex.; Tom Kaspar; Mark Prieksat, both of Ames, Iowa

[73] Assignees: Iowa State University Research Foundation, Inc., Ames, Iowa; The United States of America as represented by the United States Department of Agriculture, Washington, D.C.

[21] Appl. No.: 683,297

[22] Filed: Apr. 10, 1991

[51] Int. Cl.⁵ .............................. G01N 15/08
[52] U.S. Cl. ........................................ 73/38
[58] Field of Search ........................... 73/38, 73

[56] References Cited

U.S. PATENT DOCUMENTS

| | | | |
|---|---|---|---|
| 3,898,872 | 8/1972 | Skaling et al. | 73/73 |
| 4,478,069 | 10/1984 | Zuckerwar | 73/38 |
| 4,520,657 | 6/1985 | Marthaler | 73/73 |
| 4,773,254 | 9/1988 | Shen | 73/38 |
| 4,779,200 | 10/1988 | Bradbury et al. | 364/422 |
| 4,843,878 | 7/1989 | Purfurst et al. | 73/155 |
| 4,884,436 | 12/1989 | Ankeny et al. | 73/38 |
| 4,890,487 | 1/1990 | Dussan et al. | 73/152 |
| 4,956,993 | 9/1990 | Mehler | 73/38 |

OTHER PUBLICATIONS

Matula S. & Dirksen C. "Automated Regulating & Recording System for Cylinder Infiltrometers", pp. 299-302; *Soil Sci Soc Am J.*, vol. 53, Jan.-Feb. 1989.

Bouwer, Herman; "Intake Rate: Cylinder Infiltrometer", pp. 825-843; *Methods of Soil Analysis*, Part I. *Physical & Mineralogical Methods*, 1986 Agronomy Monograph No. 9, (2nd ed.).

*Primary Examiner*—Hezron E. Williams
*Assistant Examiner*—Michael Brock
*Attorney, Agent, or Firm*—Henderson & Sturm

[57] ABSTRACT

A ponded infiltrometer including a bubble chamber formed in a base that supports a liquid reservoir. A single valve interposed in a channel between the bubble chamber and the reservoir controls both air flow into the device and water flow out of the device. A selectively movable bubble tube communicates between the bubble chamber and the atmosphere, and the position of the lower end of the bubble tube precisely regulates the amount of ponded water in the containment ring which contacts a section of soil. The base and attached reservoir are supported and secured above the containment ring by an adjustable tripod.

21 Claims, 3 Drawing Sheets

AUTOMATED PONDED INFILTROMETER

TECHNICAL FIELD

This invention relates to devices for analyzing hydraulic characteristics of soil, and more particularly to an infiltrometer for automatically measuring saturated infiltration rates.

BACKGROUND ART

Infiltrometers have been used for many years to collect information regarding soil characteristics. These instruments are used to measure soil characteristics and properties such as sorptivity, unsaturated hydraulic conductivity, macroporosity, and others. The measurements are then used to derive information useful in determining soil hydraulic properties for studying leaching and erosion, modeling soil pore structure to estimate drainage and other characteristics, and allowing informed prediction of root growth and other factors associated with soil tilth. An automated tension infiltrometer is shown and described in U.S. Pat. No. 4,884,436 which is incorporated herein by reference.

Soil variability necessitates ponded infiltration measurements at numerous sites to accurately characterize infiltration on a field scale. Also, rapid and precise measurement of infiltration in-situ is important for characterizing soil properties. However, currently known instruments and methods used to measure ponded or saturated infiltration rates are imprecise, difficult to transport, and ill-suited for typical field situations.

Those concerned with these and other problems recognize the need for an improved ponded infiltrometer.

DISCLOSURE OF THE INVENTION

The present invention provides a ponded infiltrometer including a bubble chamber formed in a base that supports a liquid reservoir. A single valve interposed in a channel between the bubble chamber and the reservoir controls both air flow into the device and water flow out of the device. A selectively movable bubble tube communicates between the bubble chamber and the atmosphere, and the position of the lower end of the bubble tube precisely regulates the amount of ponded water in the containment ring which contacts a section of soil. The base and attached reservoir are supported and secured above the containment ring by an adjustable tripod.

The automated, self-regulating, ponded infiltrometer of the present invention is useful for measuring infiltration rates between $1 \times 10^{-8}$ and $3.7 \times 10^{-3}$ m s$^{-1}$. The infiltrometer limits to $\pm 1$ mm fluctuations in the height of water ponded in the containment ring. Flow rates are calculated from changes in water height in a water supply reservoir over time. Water height changes are measured as the difference in tension between two pressure transducers, one at the top of the water reservoir and one at the base. Advantages of the new device include accurate control of ponded water height, precise infiltration rate measurement, automated data collection, and rapid set-up and movement in the field. The infiltrometer has been used to measure infiltration directly over the base of corn (Zea mays L.) plants and in trafficked and untrafficked interrows on a Webster clay loam soil (fine-loamy, mixed, mesic Typic Haplaquolls). Infiltration rates were four to eight times greater directly over the base of corn plants than in nearby interrows.

An object of the present invention is the provision of an improved ponded infiltrometer.

Another object is to provide a ponded infiltrometer that is convenient and easy to use.

A further object of the invention is the provision of a ponded infiltrometer that includes automated data collection.

Still another object is to provide a ponded infiltrometer that allows precise measurements.

A still further object of the present invention is the provision of a ponded infiltrometer that is well suited for typical field situations.

BRIEF DESCRIPTION OF THE DRAWINGS

These and other attributes of the invention will become more clear upon a thorough study of the following description of the best mode for carrying out the invention, particularly when reviewed in conjunction with the drawings, wherein.

BEST MODE FOR CARRYING OUT THE INVENTION

Figure 1:
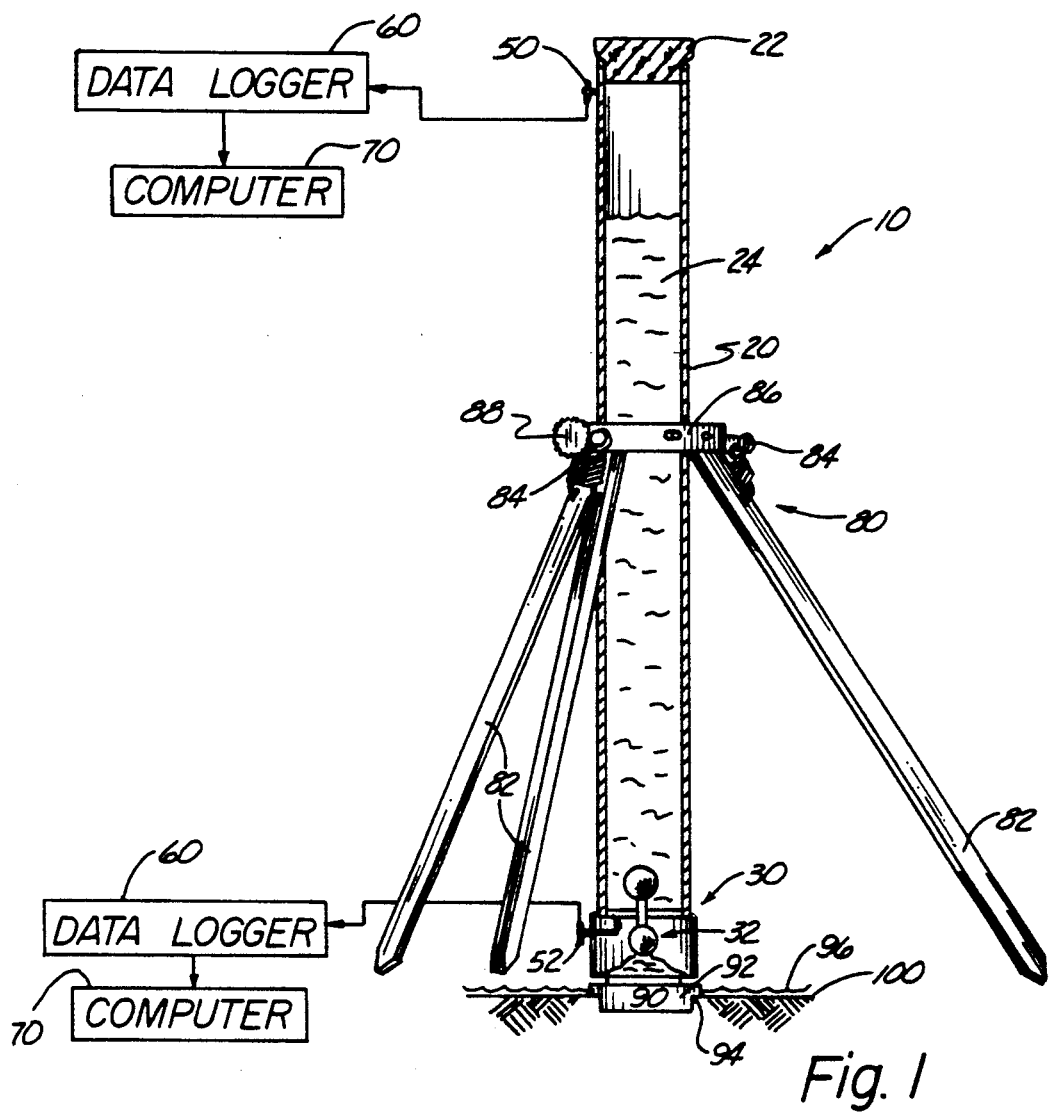
FIG. 1 is a side elevational view of the ponded infiltrometer of the present invention.

Referring now to the drawings, wherein like reference numerals designate identical or corresponding parts throughout the several views, FIG. 1 shows the ponded infiltrometer (10) of the present invention. The major components of the infiltrometer (10) are a water reservoir (20), a valved base (30), two pressure transducers (50, 52), a datalogger (60), a computer (70), and a tripod (80). The water reservoir (20) and the base (30) are constructed of polycarbonate, although other suitable materials may be used. The water reservoir (20) is a 7.62 cm diameter (0.32-cm thick) by 76.20 cm long tube. A rubber stopper (22) is used to seal the top of the reservoir (20) after filling with water (24). Pressure, created by pushing the stopper (22) into the reservoir (20), starts water flow out of the base (30) when the base valve (32) is opened.

Figure 2:
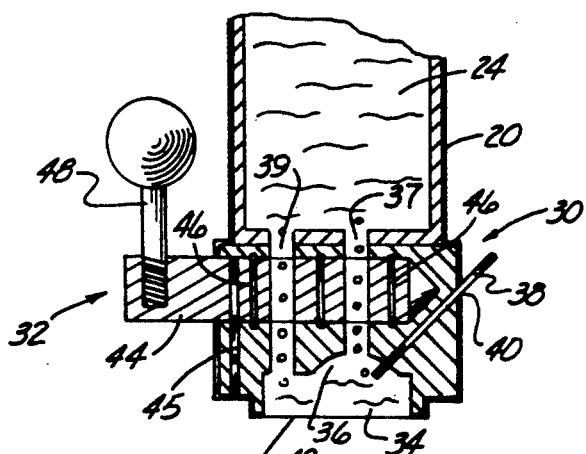
FIG. 2 is an enlarged partial side elevational view showing the bubble chamber formed in the base, and the valve that controls the air flow in and the water flow out of the infiltrometer.

As best shown in FIG. 2, the base (30) consists of a bubble chamber (34) having a raised dome section (36), a bubbling tube (38), movably received in a bubble tube opening (40), and a two-port valve (32).

The valve (32) is a plug cock valve with its two ports selectively aligned with a first channel (37) and second channel (39). The valve stem (44) is held in position by a set screw (45), and O-rings (46) provide a fluid seal. The valve (32) selectively allows or prevents fluid flow through the first and second channels (37, 39) by rotation of the valve handle (48). The bubble tube (38) regulates the height of water ponded on the soil to $\pm 1$ mm.

The bubble tube (38) is adjusted up or down within the bubble chamber (34) to raise or lower, respectively, the height of the ponded water. The valve (32) is open during measurement and is closed for movement between sites. A low impedance 325-mesh nylon filter (42) (Spex Industries, Edison, N.J.) covers the open bottom of the base. The liquid permeable nylon filter (42) prevents air from entering the device, except through the bubble tube (38).

The water reservoir (20) is attached to the base (30) with hot melt plastic glue (Stanley Tools, New Britain, Conn.), which provides an airtight seal. The 7.62 cm diameter water reservoir (20) can be replaced with a smaller diameter tube (5.08 or 2.54 cm) when low infiltration rates are expected. At low flow rates, a small diameter tube will evidence a greater change in water height, as well as better measurement precision, than will a large tube.

The device is leveled by adjusting the angle of each tripod leg (82) with the leveling screws (84). The pointed tripod legs (82) can also be pushed into the ground to stabilize the device. The water reservoir (20) and the base (30) can be moved up or down in the tripod collar (86) and then locked in place with the collar lock (88) so that the weight of the infiltrometer (10) is supported by the tripod (80) and not by the containment ring (90).

The containment ring (90) is disposed to contact and encircle a section of soil (100). The ring (90) includes an outwardly extending flange (92) having a lower face (94) disposed to contact the soil (100) and act as a depth stop for the ring (90). A section of non-porous film (96) is attached to and extends outwardly from the flange (92) to prevent excess fluid from infiltrating into the soil (100) adjacent the outer perimeter of the ring (90).

A unit change in water height in the reservoir (20) causes a unit change in tension. Thus, water flow from the reservoir can be calculated from the change in tension in the reservoir (20) over time. The infiltrometer data-collection system, which consists of two four-wire full-bridge pressure-transducers (50, 52) a data-logger (60) and a computer (70), has been described previously by Ankeny et al. (U.S. Pat. No. 4,884,436). One pressure transducer (50) is located at the top of the water reservoir (20) and the other transducer (52) in the base (30). The datalogger (60) is programmed to record paired readings of top and bottom transducers (50, 52) at regular intervals.

Also, the transducers (50, 52) may be differential pressure transducers having upper and lower parts which measure differences of pressure at upper and lower positions of the reservoir (20) and output a signal representing such differential pressure.

Figure 3:
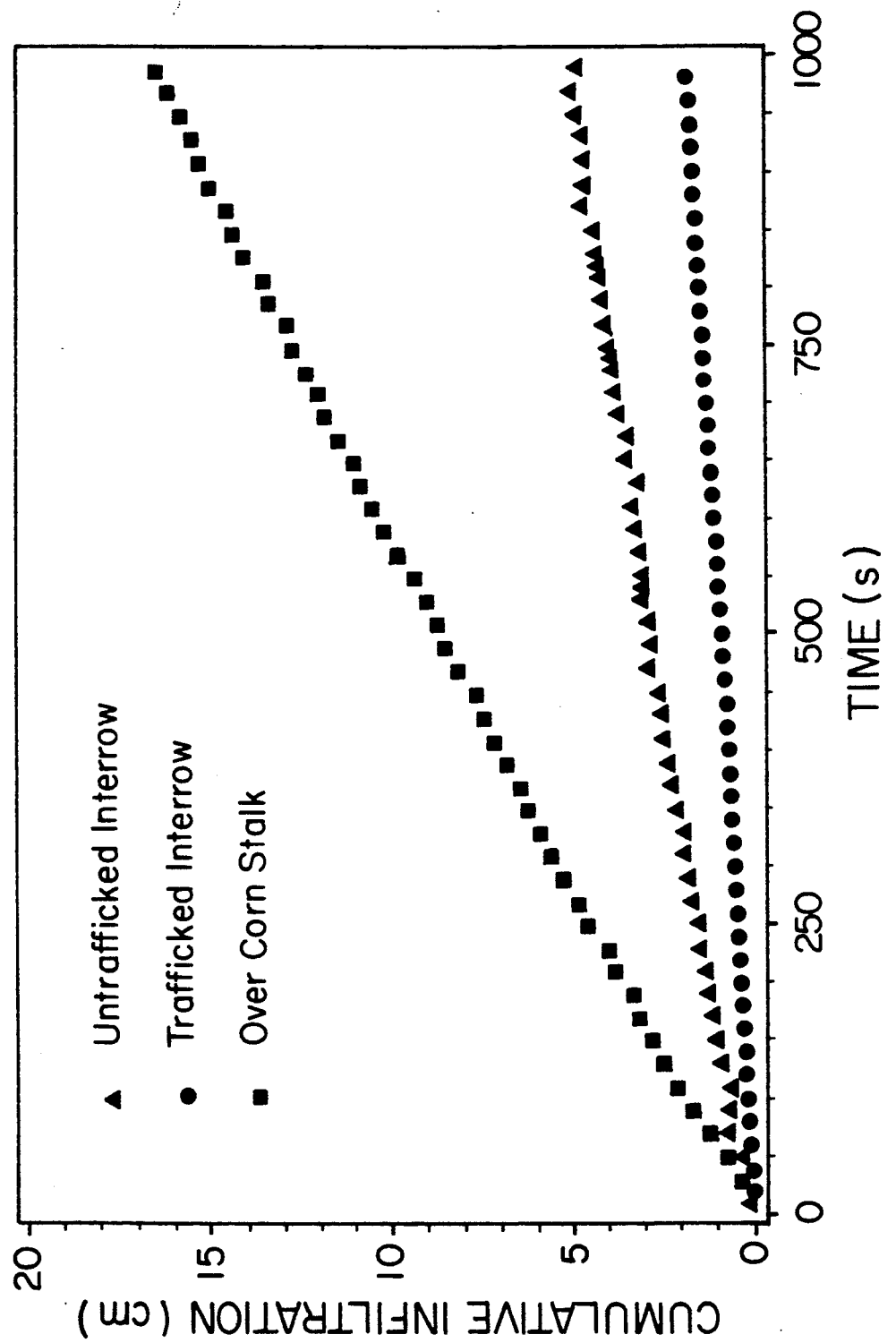
FIG. 3 is a graph illustrating cumulative infiltration over time at two interrow positions and around the base of a corn stalk.

The single ponded infiltrometer (10) was used to measure saturated infiltration directly over the base of corn plants and at two interrow positions (trafficked and untrafficked) on a Webster silty clay loam soil. FIG. 3 shows one data set collected at two interrow positions and directly over the base of a corn plant cut off at the soil surface. A 10.2 cm diameter metal containment ring (90) (0.05 cm thick; 2.50 cm high) pressed into the soil about 1 cm was used to pond water on the soil surface. Infiltration rates directly over the plant base were four and eight times higher than rates in nearby untrafficked and trafficked interrows, respectively.

Unconfined infiltration rates ranging from $2.2 \times 10^{-5}$ to $1.75 \times 10^{-4}$ m s$^{-1}$ were measured in the field. Infiltration rates in the field never exceeded the maximum water-delivery rate of the Infiltrometer (10), which was $3.0 \times 10^{-5}$ m$^3$ s$^{-1}$. This delivery rate is equivalent to an infiltration rate of $3.7 \times 10^{31\ 3}$ m s$^{-1}$ when a 10.2 cm diameter containment ring (90) is used. Using a small containment ring (90) will increase the maximum possible infiltration rate by reducing the infiltration area. Flow rates between $1 \times 10^{-8}$ and $3.7 \times 10^{-3}$ m s$^{-1}$ have been measured in the lab with the infiltrometer (10). Normally, these extreme values will not be encountered, and field infiltration measurements will fall within the laboratory range of flow rates.

Figure 4:
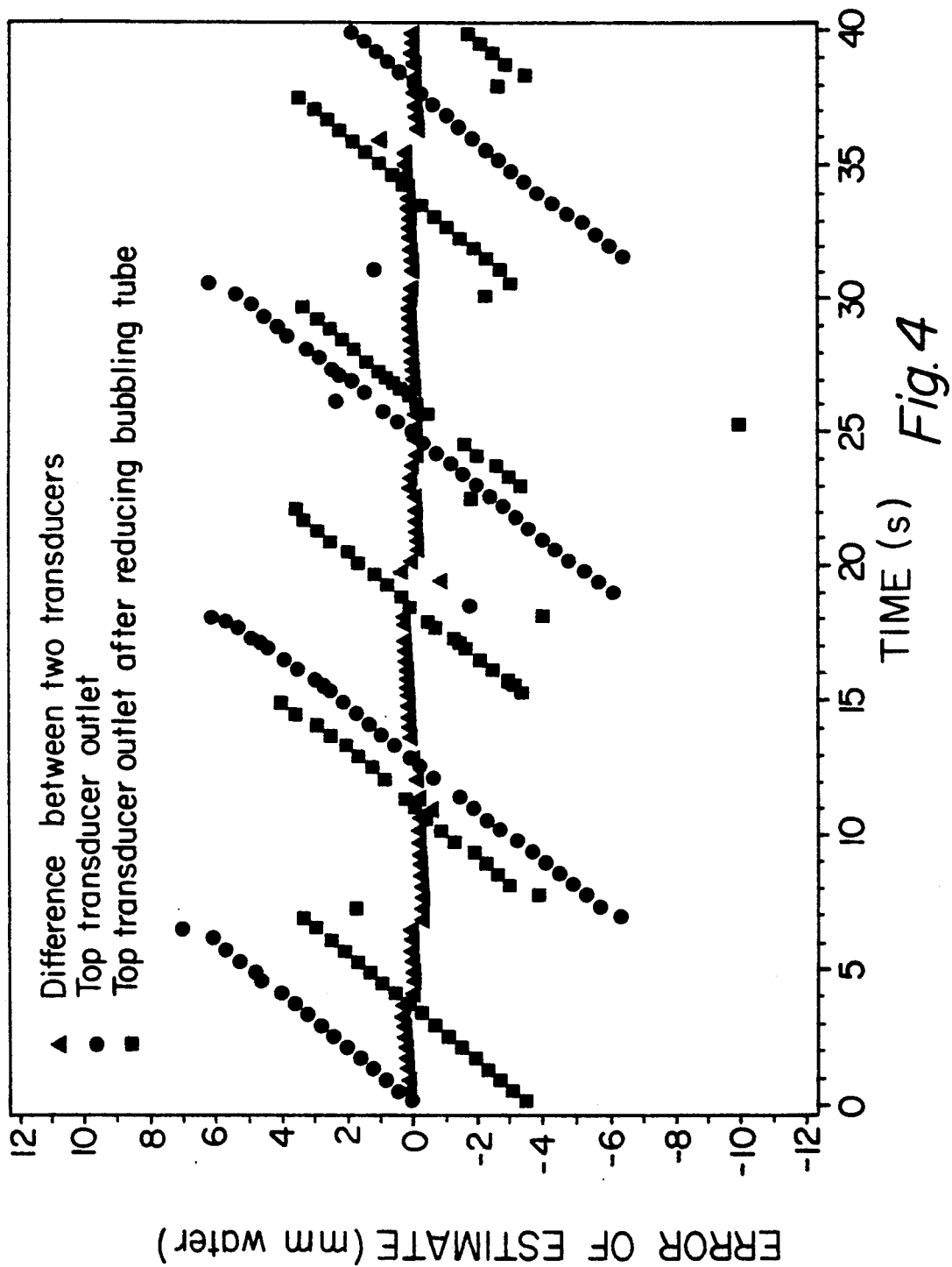
FIG. 4 is a graph illustrating tension changes, measured by one transducer and the tension difference between two transducers, in a water reservoir caused by air flowing through the device without water outflow. The diagonal lines represent data collected when bubbling tubes of different diameters (1.6 mm inside diameter, and 0.6 mm inside diameter) were used.

Water flows from the water reservoir (20) to the containment ring (90) as air flows through the bubbling tube (38) into the reservoir (20). As a bubble forms on the bubbling tube (38), tension increases in the reservoir (20), and the water level drops in the containment ring (90). When a bubble is released, tension decreases, water flows out of the reservoir (20), and the water level rises in the containment ring (90). Therefore, bubble size controls fluctuations in water reservoir tension and in water level in the containment ring (90). At high flow rates these fluctuations are negligible compared with the great changes in water-column height. At low flow rates, however, fluctuations in the height of water in the water reservoir (20) and the containment ring (90) can be greater than water-column height changes. FIG. 4 shows the results of a lab test performed by applying a slight suction to the top of the water reservoir (20), causing the device to bubble with no outflow of water. The long diagonal lines represent the tension change during bubble formation (measured by the top transducer) when a 1.6 mm interior diameter bubbling tube (38) was used. The short diagonal lines represent the tension change when the diameter of the 1.6 mm bubbling tube (38) was reduced with an 18-gauge (0.6 mm interior diameter) hypodermic needle. When the diameter of the bubbling tube (38) was reduced, so was the size of the bubbles, and the rate of bubbling increased. Small bubbles reduced fluctuations in water-reservoir tension and containment-ring water height. The standard deviation of the tension measurement also decreased from 4 to 2 mm.

Using the difference in tension between the upper transducer (50) and a lower transducer (52) eliminates the variability in tension measurements and therefore, improves precision of water flow measurements. Two transducers, however, do not affect water level fluctuations in the containment ring (90).

This automated, ponded infiltrometer (10) permits rapid, unattended measurement of in-situ infiltration to characterize soil properties. The automated ponded infiltrometer (10) is useful for characterizing the properties of agricultural soils. Because of automated data collection, measurements can be made simultaneously at multiple sites. This permits the sampling of a sufficient number of sites to overcome field variability.

Thus, it can be seen that at least all of the stated objectives have been achieved.

Obviously, many modifications and variations of the present invention are possible in light of the above teachings. It is therefore to be understood that, within the scope of the appended claims, the invention may be practiced otherwise than as specifically described.

We claim:
1. A ponded infiltrometer comprising:
   a base;
   a liquid reservoir attached to the base and disposed to hold a quantity of fluid;

a bubble chamber formed in the base and having an open bottom;

a liquid permeable member disposed over the open bottom of the bubble chamber;

an upwardly directed bubble tube opening extending between the bubble chamber and the exterior of the base;

a bubble tube received in the opening and having a lower end disposed to extend into the bubble chamber, the bubble tube being selectively movable between a raised position wherein the lower end is positioned above the bubble chamber and a lowered position wherein the lower end is positioned near the open bottom;

a first channel interconnecting the reservoir and the bubble chamber;

means for selectively controlling fluid flow between the reservoir and the bubble chamber through the first channel;

a containment ring disposed to contact a section of soil below the base;

means for supporting the base above the containment ring; and means for measuring the rate of fluid flow between the reservoir and the soil.

2. The infiltrometer of claim 1 wherein the controlling means includes a valve disposed to allow or prevent fluid flow through the first channel.

3. The infiltrometer of claim 2 wherein the valve is a plug cock valve.

4. The infiltrometer of claim 1 wherein the supporting means includes a tripod having an adjustable central collar disposed to receive and support the reservoir.

5. The infiltrometer of claim 4 wherein the central collar includes a collar lock to secure the reservoir in a position above the containment ring.

6. The infiltrometer of claim 5 wherein the tripod includes adjustable leg leveling screws to secure the reservoir in a vertical position above the containment ring.

7. The infiltrometer of claim 1 wherein the flow rate measuring means includes a first transducer operably attached to the reservoir.

8. The infiltrometer of claim 7 wherein the flow rate measuring means further includes a second transducer operably attached to the base at a position vertically spaced from the first transducer.

9. The infiltrometer of claim 7 wherein the first transducer is operably connected to a correlating recording device for recording measurements of the first transducer.

10. The infiltrometer of claim 9 further including a data logger for receiving measurements from the first transducer and for recording the measurements.

11. The infiltrometer of claim 10 further including a computer operably connected to the data logger for processing the measurements to derive soil characteristic information.

12. The infiltrometer of claim 7 wherein the first transducer is a differential pressure transducer having upper and lower ports which measure differences of pressure at upper and lower positions of the reservoir and outputs a signal representing such differential pressure.

13. The infiltrometer of claim 1 wherein said containment ring includes an outwardly extending flange having a lower face disposed to engage a soil surface disposed outwardly from the section of soil below the base.

14. The infiltrometer of claim 13 further including a section of non-porous film attached to and extending outwardly from the flange.

15. The infiltrometer of claim 1 wherein the liquid permeable member is a fine mesh filter.

16. The infiltrometer of claim 1 further including a second channel interconnecting the reservoir and the bubble chamber, the second channel being spaced from the first channel.

17. The infiltrometer of claim 16 wherein the first channel is disposed adjacent to the lower end of the bubble tube such that air bubbles from the bubble tube rise through the first channel into the reservoir.

18. The infiltrometer of claim 17 wherein the bubble chamber includes a raised dome section adjacent the bubble tube opening and the first channel, whereby enhanced flow of air bubbles directly from the bubble tube to the first channel is achieved.

19. The infiltrometer of claim 16 further including means for selectively controlling fluid flow between the reservoir and the bubble chamber through the second channel.

20. The infiltrometer of claim 19 wherein the controlling means includes a valve disposed to allow or prevent air flow through the second channel.

21. The infiltrometer of claim 20 wherein the valve is a plug cock valve.

* * * * *